US010465216B2

(12) United States Patent
Abrahamson et al.

(10) Patent No.: US 10,465,216 B2
(45) Date of Patent: Nov. 5, 2019

(54) PROCESS FOR THE PREPARATION OF (S)-2-AMINO-NON-8-ENOIC ACID

(71) Applicant: AbbVie Inc., North Chicago, IL (US)

(72) Inventors: Michael J. Abrahamson, Chicago, IL (US); Julie J. Pruyne, Gurnee, IL (US); Angelica B. Kielbus, Glenview, IL (US); John E. Lallaman, Beach Park, IL (US); Rajarathnam E. Reddy, Gurnee, IL (US); Sanjay R. Chemburkar, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 16/113,738

(22) Filed: Aug. 27, 2018

(65) Prior Publication Data

US 2019/0048372 A1 Feb. 14, 2019

Related U.S. Application Data

(62) Division of application No. 14/874,001, filed on Oct. 2, 2015, now Pat. No. 10,059,969.

(60) Provisional application No. 62/059,269, filed on Oct. 3, 2014.

(51) Int. Cl.
*C12P 13/04* (2006.01)

(52) U.S. Cl.
CPC ....... *C12P 13/04* (2013.01); *C12Y 104/01009* (2013.01)

(58) Field of Classification Search
CPC .......... C12Y 104/01009; C07C 51/377; C07C 67/343
See application file for complete search history.

(56) References Cited

U.S. PATENT DOCUMENTS

| | | | |
|---|---|---|---|
| 4,952,496 | A | 8/1990 | Studier et al. |
| 5,693,489 | A | 12/1997 | Studier et al. |
| 5,869,320 | A | 2/1999 | Studier et al. |
| 9,809,534 | B1 | 11/2017 | Lukin et al. |
| 9,809,576 | B1 | 11/2017 | Cink et al. |
| 10,113,152 | B1 | 7/2018 | Abrahamson et al. |
| 10,059,969 | B1 | 8/2018 | Abrahamson et al. |
| 10,316,338 | B1 | 6/2019 | Abrahamson et al. |
| 2011/0212504 | A1 | 9/2011 | Liu |
| 2011/0229940 | A1 | 9/2011 | Nojiri et al. |
| 2012/0070416 | A1 | 3/2012 | Or et al. |
| 2013/0096339 | A1 | 4/2013 | Asuma et al. |
| 2015/0175626 | A1 | 6/2015 | Cagulada et al. |
| 2016/0361375 | A1 | 12/2016 | Bjornson et al. |
| 2018/0057482 | A1 | 3/2018 | Cink et al. |
| 2018/0194721 | A1 | 7/2018 | Lukin et al. |
| 2018/0258451 | A1 | 9/2018 | Abrahamson et al. |

FOREIGN PATENT DOCUMENTS

| | | | |
|---|---|---|---|
| WO | WO-2008/067981 A2 | 6/2008 | |
| WO | WO-2010/030359 A2 | 3/2010 | |
| WO | WO-2010/050516 A1 | 5/2010 | |
| WO | WO-2018/144681 A1 | 8/2018 | |

OTHER PUBLICATIONS

U.S. Appl. No. 15/010,557, Abrahamson et al.
Branden et al., "Prediction, Engineering, and Design of Protein Structures," Introduction to Protein Structure, pp. 247 (1991).
Faucher, A.M. et al., "Synthesis of BILN 2061, an HCV NS3 Protease Inhibitor with Proven Antiviral Effect in Humans," Org Lett, 6(17):2901-04 (2004).
International Search Report and Written Opinion for International Application No. PCT/US18/16362 dated Jul. 6, 2018.
Kaneko et al., Q8YZN1—UniProtKB Database, May 3, 2013.
Nierman, "Complete genome sequence of Caulobacter crescentus," UniProtKB database No. Q9A6L1, 2013.
Nobili et al., "Use of 'Small but Smart' Libraries to Enhance the Enantioselectivity of an Esterase for Bacillus Stearothermophilus Towards Tetrahydrofuran-3-yl Acetate," FEBS Journal, 280(12):3084-3091 (2013).
Park et al., "Asymmetric Syntheses of iso-Boc (S)-2-Amino-8-nonenoic Acid in One Through-Process," Org Process Res Dev, 20:76-80 (2016).
Studer et al., "Residue mutations and their impact on protein structure and function: detecting beneficial and pathogenic changes," Biochem J, 449(3):581-594 (2013).
Wang, X.J. et al., "Efficient Synthesis of (S)-2-(Cyclopentyloxycarbonyl)-amino-8-nonenoic Acid: Key Building Block for BILN 2061, an HCV NS3 Protease Inhibitor," Org Process Res Dev, 11:60-3 (2007).
U.S. Appl. No. 14/873,706, AbbVie Inc.
U.S. Appl. No. 14/874,001, AbbVie Inc.
Whisstock et al., "Prediction of protein function from protein sequence and structure," Quarterly Reviews of Biophysics, 36(3):307-340 (2003).
Kisselev, "Polypeptide release factors in prokaryotes and eukaryotes: same function, different structure," Structure, 10(1):8-9 (2002).
Witkowski et al., "Conversion of a β-ketoacyl synthase to a malonyl decarboxylase by replacement of the active-site cysteine with glutamine," Biochemistry, 38(36):11643-11650 (1999).
Devos et al., "Practical limits of function prediction," Proteins: Structure, Function, and Bioinformatics, 41:98-107 (2000).

*Primary Examiner* — Kagnew H Gebreyesus
(74) *Attorney, Agent, or Firm* — Dana M. Gordon; Foley Hoag LLP

(57) ABSTRACT

Disclosed herein is a process for preparing enantioenriched (S)-2-aminonon-8-enoic acid by amination of 2-oxonon-8-enoic acid in the presence of an enzyme and an ammonia source.

6 Claims, 1 Drawing Sheet

Specification includes a Sequence Listing.

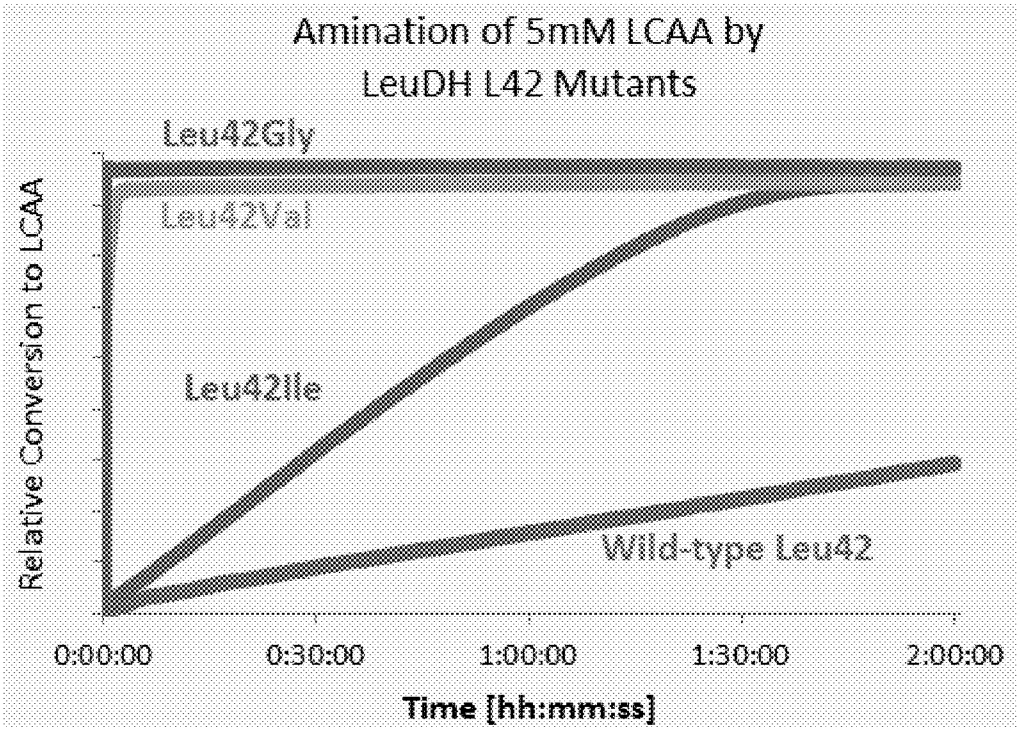
Amination of 5mM LCAA by
LeuDH L42 Mutants
Leu42Gly
Leu42Val
Leu42Ile
Wild-type Leu42
Relative Conversion to LCAA
0:00:00
0:30:00
1:00:00
1:30:00
2:00:00
Time [hh:mm:ss]

PROCESS FOR THE PREPARATION OF (S)-2-AMINO-NON-8-ENOIC ACID

RELATED APPLICATIONS

This application is a divisional of U.S. patent application Ser. No. 14/874,001, filed Oct. 2, 2015, now U.S. Pat. No. 10,059,969, which claims the benefit of priority to U.S. Provisional Patent Application Ser. No. 62/059,269, filed Oct. 3, 2014.

SEQUENCE LISTING

The instant application contains a Sequence Listing which has been submitted electronically in ASCII format and is hereby incorporated by reference in its entirety. Said ASCII copy, created on Nov. 25, 2015, is named AVR-033.01 (31941.03301) SL.txt and is 59,309 bytes in size.

BACKGROUND OF THE INVENTION

Synthesis of (S)-2-aminonon-8-enoic acid has been reported in the literature. Faucher, et al., reported a six step synthetic sequence for (S)-2-aminonon-8-enoic acid, which involves catalytic hydrogenation of an enamine substrate utilizing a DUPHOS ligand system as the key step for introduction of α-amino acid chirality (*Org. Lett.* 2004, 6, 2901-2904). Subsequently, Wang, et al., reported an enzymatic approach for the preparation of (S)-2-aminonon-8-enoic acid using acylase for the selective kinetic hydrolysis of a racemic acetamide substrate, with a theoretical step yield of 50%, in a six-step sequence (*Org. Process Res. Dev.* 2007, 11, 60-63). In 2008, an alternate approach involving a whole-cell catalytic system was disclosed for preparation of enantiomerically enriched (S)-2-aminonon-8-enoic acid from the corresponding hydantoin substrate (WO 2008/067981 A2). Subsequently, a different approach was reported (WO 2010/050516 A1; WO 2008/067981 A2) for (S)-2-aminonon-8-enoic acid, which was also based on selective kinetic hydrolysis of a racemic succinyl amide substrate using an L-succinylase enzyme (amidase), with a theoretical 50% step yield.

Previously-disclosed methods are neither efficient nor best suited for the large-scale preparation of (S)-2-aminonon-8-enoic acid, as some of them involve multiple steps, with individual steps within a sequence possessing the limitation of a maximum 50% theoretical step yield. Thus, there is a need in the art for an improved process for preparing (S)-2-aminonon-8-enoic acid.

SUMMARY OF THE INVENTION

The present invention generally relates to a process for preparing an enantioenriched, non-proteinogenic (or unnatural), long-chain amino acid (LCAA).

In one aspect, the invention relates to a process for preparing an enantioenriched 2-aminonon-8-enoic acid, comprising aminating 2-oxonon-8-enoic acid in the presence of an enzyme and an ammonia source.

In another aspect, the invention relates to a process for preparing a compound of formula (IV), comprising reacting a reagent of formula (II) with a compound of formula (III).

BRIEF DESCRIPTION OF THE FIGURE

FIG. 1 is a graph depicting the increase in reaction rates of various protein-engineered LeuDH enzymes compared to the wild-type Leu42 enzyme in the amination reaction of 5 mM LCAA substrate. The resulting reaction rate for formation of LCAA increases by approximately 1,000-fold for the mutant Leu42 variants compared to the wild-type.

DETAILED DESCRIPTION OF THE INVENTION

One aspect of the invention provides for a process for preparing an enantioenriched 2-aminonon-8-enoic acid, comprising aminating 2-aminonon-8-enoic acid in the presence of an enzyme and an ammonia source.

The process may begin with a haloalkene, such as 7-bromohept-1-ene, from which an organometallic (e.g., Grignard) reagent of formula (II) is generated, e.g., by treating the haloalkene with magnesium turnings in a solvent, such as THF. The resulting organometallic reagent may be reacted with an oxalic acid derivative, e.g., a diester of formula (III), such as diethyl oxalate, e.g., at low temperature (see, e.g., *Synthetic Commun.* 1981, 11, 943-6). The reaction may be quenched with a proton source, such as hydrochloric acid, and the desired product extracted from the resulting mixture with an organic solvent, such as dichloromethane. The crude product may be purified, for example, by silica gel ("flash") chromatography, to afford alkyl 2-oxonon-8-enoate of formula (IV).

The alkyl 2-oxonon-8-enoate may then be hydrolyzed, whether directly from the crude reaction mixture of the prior step or after purification and/or isolation. The hydrolysis may be performed under basic conditions (e.g., such as lithium hydroxide in an aqueous solvent, such as THF and water), Alternatively, the hydrolysis may be conducted under acidic conditions, such as using hydrochloric acid in an aqueous solvent, such as 1,4-dioxane and water, to afford 2-oxonon-8-enoic acid. The 2-oxonon-8-enoic acid may then be isolated from the reaction mixture, e.g., by chromatographic purification.

In some embodiments of the invention, 2-oxonon-8-enoic acid may be aminated in the presence of an enzyme, co-factors and an ammonia source to give enantioenriched (S)-2-aminonon-8-enoic acid. In certain such embodiments, the ammonia source comprises a buffered aqueous solution of ammonium chloride and ammonium hydroxide, e.g., at a pH of about 9.5. In some embodiments, the co-factors may comprise nicotinamide adenine dinucleotide (NAD), glucose and glucose dehydrogenase (GDH). For example, the NAD may be a reduced form of NAD, the GDH may be GHD-105, and the glucose may be (D)-glucose, e.g., at a concentration of about 100 mM. In certain embodiments, the amination reaction is conducted at a temperature in the range of about 37-45° C.

In certain embodiments, the LCAA substrate for the enzymatic amination reaction is present at a concentration of about 5 mM. In the amination reaction, the leucine dehydrogenase may be suspended in a volume of bacterial protein extraction reagent (BPER), or the LeuDH-containing cells may be lysed by resuspension in buffer, followed by sonication.

In some embodiments, the enzyme used in the amination reaction is a leucine dehydrogenase (LeuDH), such as LeuDH derived from *Bacillus cereus*, or another enzyme described herein. In certain embodiments, the LeuDH is a variant enzyme. For example, the LeuDH comprises at least one amino acid substitution relative to the naturally occurring enzyme, preferably including an amino acid substitution at position 42 of the amino acid sequence of the polypeptide.

In certain embodiments, the enantioenriched (S)-2-aminonon-8-enoic acid is enantioenriched to at least about 80%, 85%, 90%, 95%, 98%, or even at least about 99% enantiomeric excess (ee). In certain embodiments, the enantioenriched 2-aminonon-8-enoic acid resulting from the enzymatic amination reaction is extractively isolated from the reaction mixture, e.g., using solvent extraction methods with organic solvents, such as chloroform, tetrahydrofuran, or the like. The resulting product-containing slurry may then be filtered and then dried.

Definitions

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group. An alkyl group with two open valences is sometimes referred to as an alkylene group, such as methylene, ethylene, propylene and the like.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone.

The term "$C_{x-y}$" when used in conjunction with a chemical moiety, such as alkyl, is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal.

The term "substituted" refers to moieties having substituents replacing a hydrogen on one or more carbons or heteroatoms of the moiety. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds.

In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants.

The term "Grignard reagent" is art-recognized and refers to an alkyl-, alkenyl-, alkynyl- or aryl-magnesium halide compound of the general formula: RMgX.

The term "flash chromatography" is art-recognized and refers to a technique of silica gel column chromatography used for the purification of organic compounds as described in: Still, W. C.; Kahn, M.; Mitra, A. *J. Org. Chem.* 1978, 43(14), 2923-2925.

The present invention provides efficient methods for producing useful LCAA derivatives in high optical purity, so the optical purity of starting materials and products is sometimes described herein in terms of enantiomeric excess (ee). is a conventional method for expressing the optical purity of a mixture containing two enantiomers of a molecule in unequal amounts. The ee of such a mixture where the R enantiomer dominates, for example, is calculated as: ee=(% R−% S)/(% R+% S), where % R represents the percentage of the R enantiomer present in the mixture, and % S represents the percentage of the S enantiomer present.

Enzymes

The enzymes suitable for the methods described herein include leucine dehydrogenase (LDH) enzymes, including naturally-occurring and variant enzymes, as well as enzymatically-active fragments of these enzymes. In some embodiments, the enzyme is a LDH expressed by *Bacillus cereus*, a variant of this enzyme, or an enzymatically-active fragment of the natural or variant enzyme. An exemplary amino acid sequence for the full-length, wild-type LDH enzyme from *Bacillus cereus* is as follows:

```
                                        (SEQ ID NO: 1)
MTLEIFEYLEKYDYEQVVFCQDKESGLKAIIAIHDTTLGPALGGTRMWTY
DSEEAAIEDALRLAKGMTYKNAAAGLNLGGAKTVIIGDPRKDKSEAMFRA
LGRYIQGLNGRYITAEDVGTTVDDMDIIHEETDFVTGISPSFGSSGNPSP
VTAYGVYRGMKAAAKEAFGTDNLEGKVIAVQGVGNVAYHLCKHLHAEGAK
LIVTDINKEAVQRAVEEFGASAVEPNEIYGVECDIYAPCALGATVNDETI
PQLKAKVIAGSANNQLKEDRHGDIIHEMGIVYAPDYVINAGGVINVADEL
YGYNRERALKRVESIYDTIAKVIEISKRDGIATYVAADRLAEERIASLKN
SRSTYLRNGHDIISRR (UniProt ID No. P0A392).
```

In some embodiments, the enzyme is a LDH expressed by *Chlamydia pneumoniae*, a variant of this enzyme, or an enzymatically-active fragment of the natural or variant enzyme. An exemplary amino acid sequence for the full-length, wild-type LDH enzyme from *Chlamydia pneumoniae* is as follows:

```
                                        (SEQ ID NO: 7)
MKYSLNFKEIKIDDYERVIEVTCSKVRLHAIIAIHQTAVGPALGGVRASL
YSSFEDACTDALRLARGMTYKAIISNTGTGGGKSVIILPQDAPSLTEDML
RAFGQAVNALEGTYICAEDLGVSINDISIVAEETPYVCGIADVSGDPSIY
TAHGGFLCIKETAKYLWGSSSLRGKKIAIQGIGSVGRRLLQSLFFEGAEL
```

-continued

YVADVLERAVQDAARLYGATIVPTEEIHALECDIFSPCARGNVIRKDNLA

DLNCKAIVGVANNQLEDSSAGMMLHERGILYGPDYLVNAGGLLNVAAAIE

GRVYAPKEVLLKVEELPIVLSKLYNQSKTTGKDLVALSDSFVEDKLLAYT

S (UniProt ID No. Q9Z6Y7).

In some embodiments, the enzyme is a LDH expressed by *Thermoactinomyces intermedius*, a variant of this enzyme, or an enzymatically-active fragment of the natural or variant enzyme. An exemplary amino acid sequence for the full-length, wild-type LDH enzyme from *Thermoactinomyces intermedius* is as follows:

(SEQ ID NO: 8)

MKIFDYMEKYDYEQLVMCQDKESGLKAIICIHVTTLGPALGGMRMWTYAS

EEEAIEDALRLGRGMTYKNAAAGLNLGGGKTVIIGDPRKDKNEAMFRALG

RFIQGLNGRYITAEDVGTTVEDMDIIHEETRYVTGVSPAFGSSGNPSPVT

AYGVYRGMKAAAKEAFGDDSLEGKVVAVQGVGHVAYELCKHLHNEGAKLI

VTDINKENADRAVQEFGAEFVHPDKIYDVECDIFAPCALGAIINDETIER

LKCKVVAGSANNQLKEERHGKMLEEKGIVYAPDYVINAGGVINVADELLG

YNRERAMKKVEGIYDKILKVFEIAKRDGIPSYLAADRMAEERIEMMRKTR

STFLQDQRNLINFNNK (UniProt ID No. Q60030).

In some embodiments, the enzyme is a LDH expressed by *Bacillus subtilis*, a variant of this enzyme, or an enzymatically-active fragment of the natural or variant enzyme. An exemplary amino acid sequence for the full-length, wild-type LDH enzyme from *Bacillus subtilis* is as follows:

(SEQ ID NO: 9)

MELFKYMEKYDYEQLVFCQDEQSGLKAIIAIHDTTLGPALGGTRMWTYEN

EEAAIEDALRLARGMTYKNAAAGLNLGGGKTVIIGDPRKDKNEEMFRAFG

RYIQGLNGRYITAEDVGTTVEDMDIIHDETDYVTGISPAFGSSGNPSPVT

AYGVYRGMKAAAKAAFGTDSLEGKTIAVQGVGNVAYNLCRHLHEEGANLI

VTDINKQSVQRAVEDFGARAVDPDDIYSQDCDIYAPCALGATINDDTIKQ

LKAKVIAGAANNQLKETRHGDQIHEMGIVYAPDYVINAGGVINVADELYG

YNAERALKKVEGIYGNIERVLEISQRDGIPAYLAADRLAEERIERMRRSR

SQFLQNGHSVLSRR (UniProt ID No. P54531).

In some embodiments, the enzyme is a LDH expressed by *Bacillus licheniformis*, a variant of this enzyme, or an enzymatically-active fragment of the natural or variant enzyme. An exemplary amino acid sequence for the full-length, wild-type LDH enzyme from *Bacillus licheniformis* is as follows:

(SEQ ID NO: 10)

MELFRYMEQYDYEQLVFCQDKQSGLKAIIAIHDTTLGPALGGTRMWTYES

EEAAIEDALRLARGMTYKNAAAGLNLGGGKTVIIGDPRKDKNEEMFRAFG

RYIQGLNGRYITAEDVGTTVEDMDIIHDETDFVTGISPAFGSSGNPSPVT

AYGVYKGMKAAAKAAFGTDSLEGKTVAVQGVGNVAYNLCRHLHEEGAKLI

VTDINKEAVERAVAEFGARAVDPDDIYSQECDIYAPCALGATINDDTIPQ

-continued

LKAKVIAGAANNQLKETRHGDQIHDMGIVYAPDYVINAGGVINVADELYG

YNSERALKKVEGIYGNIERVLEISKRDRIPTYLAADRLAEERIERMRQSR

SQFLQNGHHILSRR (UniProt ID No. Q65HK5).

In some embodiments, the enzyme is a LDH expressed by *Geobacillus stearothermophilus*, a variant of this enzyme, or an enzymatically-active fragment of the natural or variant enzyme. An exemplary amino acid sequence for the full-length, wild-type LDH enzyme from *Geobacillus stearothermophilus* is as follows:

(SEQ ID NO: 11)

MELFKYMETYDYEQVLFCQDKESGLKAIIAIHDTTLGPALGGTRMWMYNS

EEEALEDALRLARGMTYKNAAAGLNLGGGKTVIIGDPRKDKNEAMFRAFG

RFIQGLNGRYITAEDVGTTVADMDIIYQETDYVTGISPEFGSSGNPSPAT

AYGVYRGMKAAAKEAFGSDSLEGKVVAVQGVGNVAYHLCRHLHEEGAKLI

VTDINKEVVARAVEEFGAKAVDPNDIYGVECDIFAPCALGGIINDQTIPQ

LKAKVIAGSADNQLKEPRHGDIIHEMGIVYAPDYVINAGGVINVADELYG

YNRERAMKKIEQIYDNIEKVFAIAKRDNIPTYVAADRMAEERIETMRKAR

SPFLQNGHHILSRRRAR (UniProt ID No. P13154).

In some embodiments, the enzyme is a LDH expressed by *Bacillus sphaericus*, a variant of this enzyme, or an enzymatically-active fragment of the natural or variant enzyme. An exemplary amino acid sequence for the full-length, wild-type LDH enzyme from *Bacillus sphaericus* is as follows:

(SEQ ID NO: 12)

MEIFKYMEKYDYEQLVFCQDEASGLKAIIAIHDTTLGPALGGARMWTYAT

EENAIEDALRLARGMTYKNAAAGLNLGGGKTVIIGDPFKDKNEEMFRALG

RFIQGLNGRYITAEDVGTTVTDMDLIHEETNYVTGISPAFGSSGNPSPVT

AYGVYRGMKAAAKEAFGTDMLEGRTISVQGLGNVAYKLCEYLHNEGAKLV

VTDINQAAIDRVVNDFGATAVAPDEIYSQEVDIFSPCALGAILNDETIPQ

LKAKVIAGSANNQLQDSRHGDYLHELGIVYAPDYVINAGGVINVADELYG

YNRERALKRVDGIYDSIEKIFEISKRDSIPTYVAANRLAEERIARVAKSR

SQFLKNEKNILNGR (UniProt ID No. Q76GS2).

The variant enzymes described herein comprise one or more amino acid substitutions, insertions, or deletions, relative to the wild-type LDH enzymes from which they were derived. In some embodiments, a variant enzyme comprises at least two (e.g., at least three, four, five, six, seven, eight, nine, 10, 15, 20, 25, 30, 35, 40, 45, 50, 55, 60, 65, 70, 75, 80, 85, 90, 95, 100, or more than 100) amino acid substitutions, deletions, or insertions, relative to the wild-type, full-length LDH enzyme from which it was derived. In some embodiments, a variant enzyme comprises no more than 150 (e.g., no more than 145, 140, 135, 130, 125, 120, 115, 110, 105, 100, 95, 90, 85, 80, 75, 70, 65, 60, 55, 50, 45, 40, 35, 30, 25, 24, 23, 22, 21, 20, 19, 18, 17, 16, 15, 14, 13, 12, 11, 10, 9, 8, 7, 6, 5, 4, 3, or 2) amino acid substitutions, deletions, or insertions, relative to the wild-type, full-length LDH enzyme from which it was derived. In some embodiments, a variant enzyme described herein, or a fragment thereof, includes an amino acid substitution at amino acid position 42 relative to SEQ ID NO:1, e.g., a substitution of leucine at position 42 for another amino acid. The amino acid at position 42, leucine, relative to SEQ ID NO:1 is one of several amino acids (GPAXGG (SEQ ID NO:3)) highly conserved among bacterial leucine dehydrogenase enzymes (FIG. 1). However, the exact position of these amino acid residues in a given enzyme varies from species to species and with any truncations or extension of the wild-type peptide. One of skill in the art would therefore appreciate that references herein to a variant enzyme (or a fragment thereof) comprising an amino acid substitution at position 42 relative to SEQ ID NO:1, include e.g., an amino acid substitution at position 43 of SEQ ID NO:7; an amino acid substitution at position 40 of SEQ ID NO:8; an amino acid substitution at position 40 of SEQ ID NO:9; an amino acid substitution at position 40 of SEQ ID NO:10; an amino acid substitution at position 40 of SEQ ID NO:11; or an amino acid substitution at position 40 of SEQ ID NO:12, i.e., position X in SEQ ID NOs:13-18.

In some embodiments, any of the variant enzymes or fragments described herein comprise the amino acid sequence NVA (SEQ ID NO:19), which corresponds to amino acids 295 to 297 of SEQ ID NO:1. In some embodiments, a variant enzyme or fragment thereof comprises the amino acid sequences depicted in SEQ ID NO:3 and SEQ ID NO:19.

As used herein, the term "conservative substitution" refers to the replacement of an amino acid present in the native sequence in a given enzyme with a naturally or non-naturally occurring amino acid having similar steric properties. Where the side-chain of the native amino acid to be replaced is either polar or hydrophobic, the conservative substitution should be with a naturally occurring amino acid, a non-naturally occurring amino acid that is also polar or hydrophobic, and, optionally, with the same or similar steric properties as the side-chain of the replaced amino acid. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. One letter amino acid abbreviations are as follows: alanine (A); arginine (R); asparagine (N); aspartic acid (D); cysteine (C); glycine (G); glutamine (Q); glutamic acid (E); histidine (H); isoleucine (I); leucine (L); lysine (K); methionine (M); phenylalanine (F); proline (P); serine (S); threonine (T); tryptophan (W), tyrosine (Y); and valine (V).

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted.

In some embodiments, the variant enzyme, or fragment thereof, comprises the amino acid sequence GPAXGG (SEQ ID NO:3), wherein X is any amino acid except for leucine. In some embodiments, X is glycine. In some embodiments, X is valine. In some embodiments, X is isoleucine. In some embodiments, X is serine. In some embodiments, X is threonine. In some embodiments, X can be, e.g., glycine, valine, isoleucine, alanine, serine, or threonine.

In some embodiments, the variant enzyme is a variant of *Bacillus cereus* LDH comprising the following amino acid sequence: MTLEIFEYLEKYDYEQVVFCQDKESGLKAIIAIHDTTLGPAXGGTRMWTYDSEEAAIED ALRLAKGMTYKNAAAGLNLGGAKTVIIGDPRKDKSEAMFRALGRYIQGLNGRYITAED VGTTVDDMDIIHEETDFVTGISPSFGSSGNPSPVTAYGVYRGMKAAAKEAFGTDNLEGK VIAVQGVGNVAYHLCKHLHAEGAKLIVTDINKEAVQRAVEEFGASAVEPNEIYGVECDI YAPCALGATVNDETIPQLKAKVIAGSANNQLKEDRHGDIIHEMGIVYAPDYVINAGGVI NVADELYGYNRERALKRVESIYDTIAKVIEISKRDGIATYVAADRLAEERIASLKNSRST YLRNGHDIISRR (SEQ ID NO:2), wherein X is any amino acid except for leucine. In some embodiments, X is glycine. In some embodiments, X is valine. In some embodiments, X is isoleucine. In some embodiments, X is alanine. In some embodiments, X is serine. In some embodiments, X is threonine.

In some embodiments, the variant enzyme comprises, or consists of, one of the following amino acid sequences:

```
(1)
                                          (SEQ ID NO: 4)
MTLEIFEYLEKYDYEQVVFCQDKESGLKAIIAIHDTTLGPAIGGTRMWTY
DSEEAAIEDALRLAKGMTYKNAAAGLNLGGAKTVIIGDPRKDKSEAMFRA
LGRYIQGLNGRYITAEDVGTTVDDMDIIHEETDFVTGISPSFGSSGNPSP
VTAYGVYRGMKAAAKEAFGTDNLEGKVIAVQGVGNVAYHLCKHLHAEGAK
LIVTDINKEAVQRAVEEFGASAVEPNEIYGVECDIYAPCALGATVNDETI
PQLKAKVIAGSANNQLKEDRHGDIIHEMGIVYAPDYVINAGGVINVADEL
YGYNRERALKRVESIYDTIAKVIEISKRDGIATYVAADRLAEERIASLKN
SRSTYLRNGHDIISRR;
(2)
                                          (SEQ ID NO: 5)
MTLEIFEYLEKYDYEQVVFCQDKESGLKAIIAIHDTTLGPAVGGTRMWTY
DSEEAAIEDALRLAKGMTYKNAAAGLNLGGAKTVIIGDPRKDKSEAMFRA
LGRYIQGLNGRYITAEDVGTTVDDMDIIHEETDFVTGISPSFGSSGNPSP
VTAYGVYRGMKAAAKEAFGTDNLEGKVIAVQGVGNVAYHLCKHLHAEGAK
LIVTDINKEAVQRAVEEFGASAVEPNEIYGVECDIYAPCALGATVNDETI
PQLKAKVIAGSANNQLKEDRHGDIIHEMGIVYAPDYVINAGGVINVADEL
YGYNRERALKRVESIYDTIAKVIEISKRDGIATYVAADRLAEERIASLKN
SRSTYLRNGHDIISRR;
(3)
                                          (SEQ ID NO: 6)
MTLEIFEYLEKYDYEQVVFCQDKESGLKAIIAIHDTTLGPAGGGTRMWTY
DSEEAAIEDALRLAKGMTYKNAAAGLNLGGAKTVIIGDPRKDKSEAMFRA
LGRYIQGLNGRYITAEDVGTTVDDMDIIHEETDFVTGISPSFGSSGNPSP
VTAYGVYRGMKAAAKEAFGTDNLEGKVIAVQGVGNVAYHLCKHLHAEGAK
LIVTDINKEAVQRAVEEFGASAVEPNEIYGVECDIYAPCALGATVNDETI
PQLKAKVIAGSANNQLKEDRHGDIIHEMGIVYAPDYVINAGGVINVADEL
YGYNRERALKRVESIYDTIAKVIEISKRDGIATYVAADRLAEERIASLKN
SRSTYLRNGHDIISRR;
or
```

-continued (4)

(SEQ ID NO: 20)

MTLEIFEYLEKYDYEQVVFCQDKESGLKAIIAIHDTTLGPAAGGTRMWTY

DSEEAAIEDALRLAKGMTYKNAAAGLNLGGAKTVIIGDPRKDKSEAMFRA

LGRYIQGLNGRYITAEDVGTTVDDMDIIHEETDFVTGISPSFGSSGNPSP

VTAYGVYRGMKAAAKEAFGTDNLEGKVIAVQGVGNVAYHLCKHLHAEGAK

LIVTDINKEAVQRAVEEFGASAVEPNEIYGVECDIYAPCALGATVNDETI

PQLKAKVIAGSANNQLKEDRHGDIIHEMGIVYAPDYVINAGGVINVADEL

YGYNRERALKRVESIYDTIAKVIEISKRDGIATYVAADRLAEERIASLKN

SRSTYLRNGHDIISRR.

In some embodiments, a variant enzyme described herein, or a fragment thereof, comprises at least ten (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:2, inclusive of the amino acid at position 42, wherein X is not leucine.

In some embodiments, a variant enzyme described herein, or a fragment thereof, comprises at least ten (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:13, inclusive of the amino acid at position 43, wherein X is not leucine. The amino acid sequence of SEQ ID NO:13 is as follows:

MKYSLNFKEIKIDDYERVIEVTCSKVRLHAIIAIHQTAVGPAXGGVRASL

YSSFEDACTDALRLARGMTYKAIISNTGTGGGKSVIILPQDAPSLTEDML

RAFGQAVNALEGTYICAEDLGVSINDISIVAEETPYVCGIADVSGDPSIY

TAHGGFLCIKETAKYLWGSSSLRGKKIAIQGIGSVGRRLLQSLFFEGAEL

YVADVLERAVQDAARLYGATIVPTEEIHALECDIFSPCARGNVIRKDNLA

DLNCKAIVGVANNQLEDSSAGMMLHERGILYGPDYLVNAGGLLNVAAAIE

GRVYAPKEVLLKVEELPIVLSKLYNQSKTTGKDLVALSDSFVEDKLLAYT

S.

In some embodiments, a variant enzyme described herein, or a fragment thereof, comprises at least ten (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:14, inclusive of the amino acid at position 40, wherein X is not leucine. The amino acid sequence of SEQ ID NO:14 is as follows:

MKIFDYMEKYDYEQLVMCQDKESGLKAIICIHVTTLGPAXGGMRMWTYAS

EEEAIEDALRLGRGMTYKNAAAGLNLGGGKTVIIGDPRKDKNEAMFRALG

RFIQGLNGRYITAEDVGTTVEDMDIIHEETRYVTGVSPAFGSSGNPSPVT

AYGVYRGMKAAAKEAFGDDSLEGKVVAVQGVGHVAYELCKHLHNEGAKLI

VTDINKENADRAVQEFGAEFVHPDKIYDVECDIFAPCALGAIINDETIER

-continued

LKCKVVAGSANNQLKEERHGKMLEEKGIVYAPDYVINAGGVINVADELLG

YNRERAMKKVEGIYDKILKVFEIAKRDGIPSYLAADRMAEERIEMMRKTR

STFLQDQRNLINFNNK.

In some embodiments, a variant enzyme described herein, or a fragment thereof, comprises at least ten (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:15, inclusive of the amino acid at position 40, wherein X is not leucine. The amino acid sequence of SEQ ID NO:15 is as follows:

MELFKYMEKYDYEQLVFCQDEQSGLKAIIAIHDTTLGPAXGGTRMWTYEN

EEAAIEDALRLARGMTYKNAAAGLNLGGGKTVIIGDPRKDKNEEMFRAFG

RYIQGLNGRYITAEDVGTTVEDMDIIHDETDYVTGISPAFGSSGNPSPVT

AYGVYRGMKAAAKAAFGTDSLEGKTIAVQGVGNVAYNLCRHLHEEGANLI

VTDINKQSVQRAVEDFGARAVDPDDIYSQDCDIYAPCALGATINDDTIKQ

LKAKVIAGAANNQLKETRHGDQIHEMGIVYAPDYVINAGGVINVADELYG

YNAERALKKVEGIYGNIERVLEISQRDGIPAYLAADRLAEERIERMRRSR

SQFLQNGHSVLSRR.

In some embodiments, a variant enzyme described herein, or a fragment thereof, comprises at least ten (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:16, inclusive of the amino acid at position 40, wherein X is not leucine. The amino acid sequence of SEQ ID NO:16 is as follows:

MELFRYMEQYDYEQLVFCQDKQSGLKAIIAIHDTTLGPAXGGTRMWTYES

EEAAIEDALRLARGMTYKNAAAGLNLGGGKTVIIGDPRKDKNEEMFRAFG

RYIQGLNGRYITAEDVGTTVEDMDIIHDETDFVTGISPAFGSSGNPSPVT

AYGVYKGMKAAAKAAFGTDSLEGKTVAVQGVGNVAYNLCRHLHEEGAKLI

VTDINKEAVERAVAEFGARAVDPDDIYSQECDIYAPCALGATINDDTIPQ

LKAKVIAGAANNQLKETRHGDQIHDMGIVYAPDYVINAGGVINVADELYG

YNSERALKKVEGIYGNIERVLEISKRDRIPTYLAADRLAEERIERMRQSR

SQFLQNGHHILSRR.

In some embodiments, a variant enzyme described herein, or a fragment thereof, comprises at least ten (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:17, inclusive of the amino acid at position 40, wherein X is not leucine. The amino acid sequence of SEQ ID NO:17 is as follows:

```
MELFKYMETYDYEQVLFCQDKESGLKAIIAIHDTTLGPAXGGTRMWMYNS

EEEALEDALRLARGMTYKNAAAGLNLGGGKTVIIGDPRKDKNEAMFRAFG

RFIQGLNGRYITAEDVGTTVADMDIIYQETDYVTGISPEFGSSGNPSPAT

AYGVYRGMKAAAKEAFGSDSLEGKVVAVQGVGNVAYHLCRHLHEEGAKLI

VTDINKEVVARAVEEFGAKAVDPNDIYGVECDIFAPCALGGIINDQTIPQ

LKAKVIAGSADNQLKEPRHGDIIHEMGIVYAPDYVINAGGVINVADELYG

YNRERAMKKIEQIYDNIEKVFAIAKRDNIPTYVAADRMAEERIETMRKAR

SPFLQNGHHILSRRRAR.
```

In some embodiments, a variant enzyme described herein, or a fragment thereof, comprises at least 10 (e.g., at least 11, 12, 13, 14, 15, 20, 25, 30, 35, 40, 45, 50, 55, 60, 65, 70, 75, 80, 85, 90, 95, 100, 105, 110, 115, 120, 130, 140, 150, 160, 170, 180, 190, 200, 210, 220, 230, 240, 250, 260, 270, 280, 290, or 300 or more) consecutive amino acids of SEQ ID NO:18, inclusive of the amino acid at position 40, wherein X is not leucine. The amino acid sequence of SEQ ID NO:18 is as follows:

```
MEIFKYMEKYDYEQLVFCQDEASGLKAIIAIHDTTLGPAXGGARMWTYAT

EENAIEDALRLARGMTYKNAAAGLNLGGGKTVIIGDPFKDKNEEMFRALG

RFIQGLNGRYITAEDVGTTVTDMDLIHEETNYVTGISPAFGSSGNPSPVT

AYGVYRGMKAAAKEAFGTDMLEGRTISVQGLGNVAYKLCEYLHNEGAKLV

VTDINQAAIDRVVNDFGATAVAPDEIYSQEVDIFSPCALGAILNDETIPQ

LKAKVIAGSANNQLQDSRHGDYLHELGIVYAPDYVINAGGVINVADELYG

YNRERALKRVDGIYDSIEKIFEISKRDSIPTYVAANRLAEERIARVAKSR

SQFLKNEKNILNGR.
```

In some embodiments of any of the variants described herein, X is glycine, isoleucine, valine, or alanine. In some embodiments, X is serine. In some embodiments, X is threonine.

In some embodiments, a variant enzyme described herein, or a fragment thereof, has an amino acid sequence that is at least 80 (e.g., at least 81, 82, 83, 84, 85, 86, 87, 88, 89, 90, 91, 92, 93, 94, 95, 96, 97, 98, or 99) % identical to: (i) amino acids 6 to 238 of SEQ ID NO:2; (ii) amino acids 7 to 237 of SEQ ID NO:13; (iii) amino acids 4 to 236 of SEQ ID NO:14; (iv) amino acids 4 to 236 of SEQ ID NO:15; (v) amino acids 4 to 236 of SEQ ID NO:16; (vi) amino acids 4 to 236 of SEQ ID NO:17; or (vii) amino acids 4 to 236 of SEQ ID NO:18, with the proviso that the variant enzyme or fragment thereof comprises the amino acid sequence at position X, whether X is leucine, or in certain preferred embodiments is not leucine. In some embodiments, the variant enzyme or fragment thereof comprises the amino acid sequence depicted in SEQ ID NO:3, wherein X is leucine or, in some preferred embodiments, is not leucine.

In some embodiments, a variant enzyme described herein, or a fragment thereof, has an amino acid sequence that is at least 80 (e.g., at least 81, 82, 83, 84, 85, 86, 87, 88, 89, 90, 91, 92, 93, 94, 95, 96, 97, 98, or 99) % identical to: (i) amino acids 6 to 298 of SEQ ID NO:2; (ii) amino acids 7 to 297 of SEQ ID NO:13; (iii) amino acids 4 to 296 of SEQ ID NO:14; (iv) amino acids 4 to 296 of SEQ ID NO:15; (v) amino acids 4 to 296 of SEQ ID NO:16; (vi) amino acids 4 to 296 of SEQ ID NO:17; or (vii) amino acids 4 to 296 of SEQ ID NO:18, with the proviso that the variant enzyme or fragment thereof comprises the amino acid sequence at position X, and X is not leucine. In some embodiments, the variant enzyme or fragment thereof comprises the amino acid sequence depicted in SEQ ID NO:3, wherein X is not leucine.

Percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software, such as BLAST software or ClustalW2 (above). Appropriate parameters for measuring alignment, including any algorithms needed to achieve maximal alignment over the full-length of the sequences being compared can be determined by known methods.

Leucine dehydrogenase from *B. cereus* exists in solution as a homo-octomer, with each subunit folding into two domains, and separated by a deep cleft. See Baker et al. (1995) *Current Biol* 3:693-705, which describes the crystal structure of leucine dehydrogenase from *B. sphaericus* (SEQ ID NO:12). The quaternary structure of the complex adopts the shape of a hollow cylinder. Leucine dehydrogenase comprises both a dehydrogenase superfamily domain (e.g., amino acids 10 to 130) and a nicotinamide adenine dinucleotide-cofactor binding domain (e.g., amino acids 150 to 350). In some embodiments, a variant enzyme or enzymatically-active fragment described herein retains at least 5 (e.g., at least 10, 15, 20, 25, 30, 35, 40, 45, 50, 55, 60, 65, 70, 75, 80, 85, 90, 95, or 100) % of the ability of the corresponding full-length, wild-type LDH enzyme from which the variant or fragment was derived to bind to a nucleotide cofactor (e.g., NAD or NADH). Methods for detecting or measuring the interaction between NAD and NAD-dependent enzymes are known in the art and described in, e.g., Kovar and Klukanova (1984) *Biochim Biophys Acta* 788(1):98-109 and in Lesk (1995) *Curr Opin Struct Biol* 5(6):775-783.

As described above, the variant enzyme described herein, as well as enzymatically-active fragments thereof, possess an enzymatic activity capable of reductive amination of an aliphatic keto acid (e.g., aliphatic 2-keto acids). For example, such enzymes convert 2-oxonon-8-enoic acid, in the presence of an ammonia source, to LCAA, e.g., (S)-LCAA. In some embodiments, a variant enzyme, or enzymatically-active fragment thereof, retains at least 5 (e.g., at least 10, 15, 20, 25, 30, 35, 40, 45, 50, 55, 60, 65, 70, 75, 80, 85, 90, 95, or 100) % of the ability of the corresponding full-length, wild-type LDH enzyme from which the variant or fragment was derived to convert 2-oxonon-8-enoic acid, in the presence of an ammonia source, to LCAA. In some embodiments, a variant enzyme, or enzymatically-active fragment thereof, retains at least 5 (e.g., at least 10, 15, 20, 25, 30, 35, 40, 45, 50, 55, 60, 65, 70, 75, 80, 85, 90, 95, or 100) % of the ability of full-length, wild-type *Bacillus cereus* LDH octomer complex to convert 2-oxonon-8-enoic acid, in the presence of an ammonia source, to LCAA, e.g., under the assay conditions described and exemplified in the working examples.

In some embodiments, a variant enzyme, or enzymatically-active fragment thereof, possesses enhanced ability to convert 2-oxonon-8-enoic acid, in the presence of an ammonia source, to LCAA, relative to the activity of full-length, wild-type *Bacillus cereus* LDH. For example, the variant enzyme or enzymatically-active fragment thereof can have at least a 5 (e.g., 10, 15, 20, 25, 30, 35, 40, 45, 50, 55, 60, 65, 70, 75, 80, 85, 90, 95, or 100) % greater activity (e.g., reaction rate) than full-length, wild-type *Bacillus cereus* LDH to convert 2-oxonon-8-enoic acid, in the presence of an ammonia source, to LCAA. In some embodiments, the activity (e.g., the reaction rate) of the variant enzyme or enzymatically-active fragment thereof is at least 1.5 (e.g., at least 2, 2.5, 3, 4, 5, 6, 7, 8, 9, 10, 20, 30, 40, 50, 100, 150, 200, 500, or even 1000) times greater than that of full-length, wild-type *Bacillus cereus* LDH, e.g., under the conditions described and exemplified in the working examples. Exemplary variant enzymes exhibiting enhanced activity relative to full-length, wild-type *B. cereus* LDH include the L42I, L42V, L42G, and L42A variant enzymes having amino acid sequences: SEQ ID NOs:4, 5, 6, and 20, respectively.

Although the invention herein is described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Contemplated equivalents of the compounds described above include compounds which otherwise correspond thereto, and which have the same general properties thereof. In general, the compounds of the present invention may be prepared by the methods illustrated in the general reaction schemes as, for example, described below, or by modifications thereof, using readily available starting materials, reagents and synthesis procedures. In these reactions, it is also possible to make use of variants which are in themselves known, but are not mentioned here.

EXEMPLIFICATION

Synthetic Protocols:

Chemistry Material and Methods.

All solvents and reagents were purchased from commercial and used without further purification. $^1H$ and $^{13}C$ NMR spectra were recorded on a Varian Gemini spectrometer (400 MHz) using $CDCl_3$ or DMSO-$d_6$ and referenced to the peak for tetramethylsilane (TMS) and the chemical shifts (δ) were reported in hertz (Hz). Mass spectrometry was performed on a ThermoFinnigan LCQ DECA XP quadrupole ion trap mass spectrometer utilizing positive-ion Atmospheric Pressure Chemical Ionization [APCI(+)]. High resolution mass determinations were carried out on an Agilent LC/MSDTOF instrument using negative-ion electrospray [$ESI^{(-)}$]. Thin-layer chromatography (TLC) was performed on pre-coated TLC Silica Gel 60 $F_{254}$ 5×10 cm plates and visualized with short-wave UV light (254 nm) or potassium permanganate strain, and solvent ratios reported. Column chromatography was performed on silica gel, Merck grade 60 (70-230 mesh). All compounds reported here had a purity of >90% as determined by high-performance liquid chromatography (HPLC) analysis using Shimadzu LC-20 or Agilent 1200 systems equipped with Supelcosil, LC-18-DB, 250×4.6 mm, 5 μm column and UV absorption was monitored at 210 nm. Injection volume was 5 μL and HPLC gradient solvent system (Mobile phase A: Water-0.05% Formic acid and Mobile Phase B: Acetonitrile-0.05% Formic acid) went from 5% to 95% Mobile Phase B in 10 min and continued for 20 min with flow rate of 1.0 mL/min.

Example 1

Ethyl 2-oxonon-8-enoate (5)

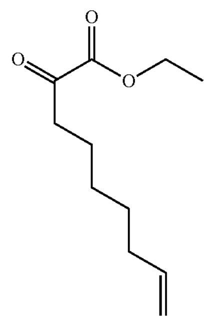

A clean, dry, 1 L 3-neck flask equipped with a stir bar and nitrogen inlet was charged with magnesium turnings (10.31 g, 0.4241 mol, 1.5 equiv.) and ~0.1 mg of iodine, and the flask was purged with nitrogen for 5 minutes. 750 mL of anhydrous THF [15 mL/g of 7-bromohept-1-ene (3)] was charged and stirring was initiated. 7-Bromohept-1-ene (3, 50.02 g, 0.2824 mol, 1.0 equiv.) was slowly added drop wise over 10-15 minutes under nitrogen. During this period, the pink color of iodine disappeared during initial stages, the reaction was found to be slightly exothermic, and the temperature of the contents was raised from an initial ambient (20-23° C.) to about 31° C. After the addition was complete, the resulting pale gray color solution was cooled to room temp (23° C.) and stirring was continued for an additional 2.5 h under nitrogen to form the Grignard reagent (7-hept-1-ene magnesium bromide).

Into a separate 2 L dry three neck RB flask equipped with a mechanical stirrer, thermocouple and an addition funnel with nitrogen inlet, diethyl oxalate (4, 82.61 g 0.5642 mol, 2.0 equiv.) and 750 mL of anhydrous THF [15 mL/g of 7-bromo-1-pentene (3)] were charged under nitrogen. The mixture was cooled to below −20° C. temperature (Jacket temperature: −23° C.) with stirring. The Grignard reagent (7-hept-1-ene magnesium bromide), which was prepared as described above, was transferred using a cannula into a side-arm addition funnel set on top of the 2 L RB flask. The reagent was added drop wise slowly into diethyl oxalate-THF solution over 1 h 50 min, while maintaining the jacket temperature below −23° C. During the addition of the Grignard reagent, the reaction was found to be exothermic and the internal temperature was raised to maximum of −18° C. After the addition was complete, the mixture was warmed to −15° C., and the progress of the reaction was monitored by HPLC. After 3 h at −15° C., the reaction mixture was warmed to −10° C., quenched with 3N hydrochloric acid solution and the final pH was adjusted to 1.4-1.6 by drop wise addition. During the quench, the internal temperature rose to −6.7° C. due to an exotherm while, the jacket temperature was maintained at −12° C. The mixture was stirred for an additional 10 min and the pH was re-checked and confirmed to be approximately, 1.7-1.8. The mixture was warmed to 22° C., and the pH was again re-checked (pH=2.8) and re-adjusted to pH=1.2 with 3N hydrochloric acid solution. A total of 81 mL of 3N hydrochloric acid solution was used for quench and pH adjustment. Agitation was stopped and the layers allowed to settle. The organic phase was separated, and the bottom aqueous layer was back-extracted with dichloromethane (1×100 mL). The combined organic phases were concentrated on a rotary evaporator (Bath temperature: 45° C./Vacuum) to give the crude product as a yellow oil. The crude product was dissolved in 200 mL of dichloromethane (some solids/salts were present) and 200 mL water. The bottom aqueous phase was separated and back-extracted with dichloromethane (2×200 mL). The combined organic phases were dried over anhydrous magnesium sulfate (25 g), filtered and concentrated on a rotary evaporator (bath temperature: 45° C., under vacuum), to afford a pale yellow viscous as oil. The crude product was purified by flash chromatography in four equal portions, with each portion dissolved in about 25 mL of dichloromethane for loading onto a silica gel column and eluted using 5-10% ethyl acetate in hexanes. The selected fractions were combined and concentrated on a rotary evaporator (bath temperature: 45° C., under vacuum), and further dried under vacuum (<5 mm/Hg) at ambient temperature for 4 h to afford 36.49 g of ethyl 2-oxonon-8-enoate (5) in 65.2% yield as colorless oil.

Example 2

2-Oxonon-8-enoic Acid (6)

6

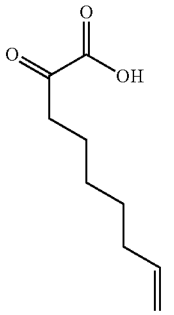

Ethyl-2-oxonon-8-enoate (5, 12.02 g, 0.0606 mol, 1.0 equiv.) and 1,4-dioxane (120 mL) were charged into a 500 mL jacketed flask, equipped with a mechanical stirrer and thermocouple. Conc. hydrochloric acid (40.9 mL, 0.4909 mol, 8.1 equiv.) was slowly added with stirring over 1-2 minutes, and the mixture was heated to 50° C. Progress of the reaction was monitored by HPLC. After 5 h at 50° C., the mixture was cooled to room temperature (22° C.) and the pH was adjusted to 9.3 using 10% (w/v) aqueous sodium carbonate solution (300 mL). The resulting solution was washed with methyl tert-butyl ether (2×250 mL) and acidified to pH=1.3 using 3 N hydrochloric acid solution (58 mL). The acidified mixture was extracted with methyl tert-butyl ether (2×150 mL). The combined organic phase was dried using anhydrous magnesium sulfate (8 g), filtered and concentrated on a rotary evaporator (bath temperature: 40° C. under vacuum). The resulting product was further dried under vacuum (<5 mm/Hg) at ambient temperature overnight for 14 h to afford 8.69 g of 2-oxonon-8-enoic acid (6) in 84.4% yield as colorless oil.

Example 3

(S)-2-Aminonon-8-enoic Acid (2)

(S)-2

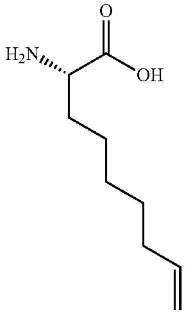

In a dry 500 mL baffled culture shake flask, 2-oxonon-8-enoic acid (6, 2.54 g, 0.0149 mol, 1.0 equiv.), D-glucose (2.75 g, 0.01531 mol, 1.03 equiv.), nicotinamide adenine dinucleotide ($NAD^+$, 0.103 g, 0.00016 mol, 0.0107 equiv.), and glucose dehydrogenase (GDH-105, 0.075 g; or any equivalent GDH) were suspended in 142 mL of 2 M ammonium chloride and ammonium hydroxide buffer solution (pH: 9.5). To this mixture, a solution of leucine dehydrogenase (LeuDH) pellet (Original culture volume: 75 mL) suspended in 7.5 mL of bacterial protein extraction reagent (BPER) was added. (Alternatively, the LeuDH pellet may be lysed via sonication). The final volume of the reaction was 150 mL with a pH of 9.0. The mixture was agitated at 37° C. temperature on a shaker. Progress of the reaction was monitored by HPLC, and after 24 h, the reaction was deemed complete. The reaction work-up procedure was as follows:

The enzymatic reaction mixture was diluted with chloroform (100 mL), and the mixture was stirred at ambient temperature (19-23° C.) for 1 h and the mixture allowed to settle overnight for 12 h. The bottom organic phase was separated from the upper aqueous phase containing solids as suspension/slurry, and the aqueous phase was filtered using Buchner funnel and Whatman filter paper (Number 1) under vacuum. The wet cake was washed with chloroform (1×20 mL) and dried at under vacuum at 23° C. for 14 h. to afford 1.93 g of (S)-2-Aminonon-8-enoic acid (2) as colorless solid in 87.3% yield and >99% enantiomeric excess.

EQUIVALENTS & INCORPORATION BY REFERENCE

It is understood that the examples and embodiments described herein are for illustrative purposes only and that various modifications or changes in light thereof will be suggested to persons skilled in the art and are included within the spirit and purview of this application and scope of the appended claims. All publications, patents, and patent applications cited herein are hereby incorporated by reference in their entirety for all purposes.

We claim:

1. A method for preparing a compound of formula (IV):

Formula (IV)

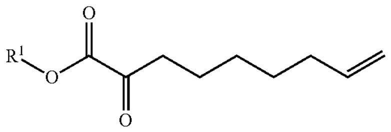

wherein $R^1$ is lower alkyl;

comprising reacting a reagent of formula (II) with a compound of formula (III),

Formula (II)

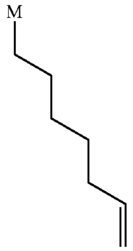

-continued

Formula (III)

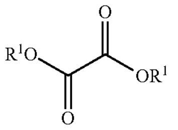

wherein independently for each occurrence $R^1$ is lower alkyl; and M is selected from Li, MgCl, MgBr, and MgI.

2. The method of claim 1, wherein $R^1$ is ethyl.

3. The method of claim 1, wherein M is MgBr.

4. The method of claim 1, wherein $R^1$ is ethyl; and M is MgBr.

5. The method of claim 1, further comprising hydrolyzing the compound of formula (IV) to produce 2-oxonon-8-enoic acid.

6. The method of claim 2, further comprising aminating the 2-oxonon-8-enoic acid in the presence of an enzyme and an ammonia source to produce enantioenriched 2-aminonon-8-enoic acid;

wherein the enzyme is a leucine dehydrogenase (LeuDH) from *Bacillus cereus;* the ammonia source comprises an ammonium chloride or ammonium hydroxide buffer solution; and the LeuDH is a wild type LeuDH or a mutant LeuDH having a mutation at position 42 of the LeuDH amino acid sequence.

* * * * *

SEQUENCE LISTING

```
<160> NUMBER OF SEQ ID NOS: 20

<210> SEQ ID NO 1
<211> LENGTH: 366
```

```
<212> TYPE: PRT
<213> ORGANISM: Bacillus cereus

<400> SEQUENCE: 1

Met Thr Leu Glu Ile Phe Glu Tyr Leu Glu Lys Tyr Asp Tyr Glu Gln
1               5                   10                  15

Val Val Phe Cys Gln Asp Lys Glu Ser Gly Leu Lys Ala Ile Ile Ala
            20                  25                  30

Ile His Asp Thr Thr Leu Gly Pro Ala Leu Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365


<210> SEQ ID NO 2
<211> LENGTH: 366
<212> TYPE: PRT
<213> ORGANISM: Artificial Sequence
```

-continued

<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: Any amino acid except Leu

<400> SEQUENCE: 2

```
Met Thr Leu Glu Ile Phe Glu Tyr Leu Glu Lys Tyr Asp Tyr Glu Gln
1               5                   10                  15

Val Val Phe Cys Gln Asp Lys Glu Ser Gly Leu Lys Ala Ile Ile Ala
            20                  25                  30

Ile His Asp Thr Thr Leu Gly Pro Ala Xaa Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365
```

-continued

```
<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid except Leu

<400> SEQUENCE: 3

Gly Pro Ala Xaa Gly Gly
1               5


<210> SEQ ID NO 4
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Thr Leu Glu Ile Phe Glu Tyr Leu Glu Lys Tyr Asp Tyr Glu Gln
1               5                   10                  15

Val Val Phe Cys Gln Asp Lys Glu Ser Gly Leu Lys Ala Ile Ile Ala
            20                  25                  30

Ile His Asp Thr Thr Leu Gly Pro Ala Ile Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270
```

```
Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365


<210> SEQ ID NO 5
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Thr Leu Glu Ile Phe Glu Tyr Leu Glu Lys Tyr Asp Tyr Glu Gln
1               5                   10                  15

Val Val Phe Cys Gln Asp Lys Glu Ser Gly Leu Lys Ala Ile Ile Ala
            20                  25                  30

Ile His Asp Thr Thr Leu Gly Pro Ala Val Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
```

```
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365


<210> SEQ ID NO 6
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Thr Leu Glu Ile Phe Glu Tyr Leu Glu Lys Tyr Asp Tyr Glu Gln
1               5                   10                  15

Val Val Phe Cys Gln Asp Lys Glu Ser Gly Leu Lys Ala Ile Ile Ala
            20                  25                  30

Ile His Asp Thr Thr Leu Gly Pro Ala Gly Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255
```

-continued

```
Val Ile Ala Gly Ser Ala Asn Asn Gln Leu Lys Glu Asp Arg His Gly
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365


<210> SEQ ID NO 7
<211> LENGTH: 351
<212> TYPE: PRT
<213> ORGANISM: Chlamydia pneumoniae

<400> SEQUENCE: 7

Met Lys Tyr Ser Leu Asn Phe Lys Glu Ile Lys Ile Asp Asp Tyr Glu
1               5                   10                  15

Arg Val Ile Glu Val Thr Cys Ser Lys Val Arg Leu His Ala Ile Ile
            20                  25                  30

Ala Ile His Gln Thr Ala Val Gly Pro Ala Leu Gly Gly Val Arg Ala
        35                  40                  45

Ser Leu Tyr Ser Ser Phe Glu Asp Ala Cys Thr Asp Ala Leu Arg Leu
    50                  55                  60

Ala Arg Gly Met Thr Tyr Lys Ala Ile Ile Ser Asn Thr Gly Thr Gly
65                  70                  75                  80

Gly Gly Lys Ser Val Ile Ile Leu Pro Gln Asp Ala Pro Ser Leu Thr
                85                  90                  95

Glu Asp Met Leu Arg Ala Phe Gly Gln Ala Val Asn Ala Leu Glu Gly
            100                 105                 110

Thr Tyr Ile Cys Ala Glu Asp Leu Gly Val Ser Ile Asn Asp Ile Ser
        115                 120                 125

Ile Val Ala Glu Glu Thr Pro Tyr Val Cys Gly Ile Ala Asp Val Ser
    130                 135                 140

Gly Asp Pro Ser Ile Tyr Thr Ala His Gly Gly Phe Leu Cys Ile Lys
145                 150                 155                 160

Glu Thr Ala Lys Tyr Leu Trp Gly Ser Ser Ser Leu Arg Gly Lys Lys
                165                 170                 175

Ile Ala Ile Gln Gly Ile Gly Ser Val Gly Arg Arg Leu Leu Gln Ser
            180                 185                 190

Leu Phe Phe Glu Gly Ala Glu Leu Tyr Val Ala Asp Val Leu Glu Arg
        195                 200                 205

Ala Val Gln Asp Ala Ala Arg Leu Tyr Gly Ala Thr Ile Val Pro Thr
    210                 215                 220

Glu Glu Ile His Ala Leu Glu Cys Asp Ile Phe Ser Pro Cys Ala Arg
225                 230                 235                 240

Gly Asn Val Ile Arg Lys Asp Asn Leu Ala Asp Leu Asn Cys Lys Ala
                245                 250                 255

Ile Val Gly Val Ala Asn Asn Gln Leu Glu Asp Ser Ser Ala Gly Met
            260                 265                 270
```

```
Met Leu His Glu Arg Gly Ile Leu Tyr Gly Pro Asp Tyr Leu Val Asn
        275                 280                 285

Ala Gly Gly Leu Leu Asn Val Ala Ala Ala Ile Glu Gly Arg Val Tyr
    290                 295                 300

Ala Pro Lys Glu Val Leu Leu Lys Val Glu Glu Leu Pro Ile Val Leu
305                 310                 315                 320

Ser Lys Leu Tyr Asn Gln Ser Lys Thr Thr Gly Lys Asp Leu Val Ala
                325                 330                 335

Leu Ser Asp Ser Phe Val Glu Asp Lys Leu Leu Ala Tyr Thr Ser
            340                 345                 350


<210> SEQ ID NO 8
<211> LENGTH: 366
<212> TYPE: PRT
<213> ORGANISM: Thermoactinomyces intermedius

<400> SEQUENCE: 8

Met Lys Ile Phe Asp Tyr Met Glu Lys Tyr Asp Tyr Glu Gln Leu Val
1               5                   10                  15

Met Cys Gln Asp Lys Glu Ser Gly Leu Lys Ala Ile Ile Cys Ile His
            20                  25                  30

Val Thr Thr Leu Gly Pro Ala Leu Gly Gly Met Arg Met Trp Thr Tyr
        35                  40                  45

Ala Ser Glu Glu Glu Ala Ile Glu Asp Ala Leu Arg Leu Gly Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Ala Met Phe
                85                  90                  95

Arg Ala Leu Gly Arg Phe Ile Gln Gly Leu Asn Gly Arg Tyr Ile Thr
            100                 105                 110

Ala Glu Asp Val Gly Thr Thr Val Glu Asp Met Asp Ile Ile His Glu
        115                 120                 125

Glu Thr Arg Tyr Val Thr Gly Val Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Glu Ala Phe Gly Asp Asp Ser Leu Glu Gly Lys Val Val
                165                 170                 175

Ala Val Gln Gly Val Gly His Val Ala Tyr Glu Leu Cys Lys His Leu
            180                 185                 190

His Asn Glu Gly Ala Lys Leu Ile Val Thr Asp Ile Asn Lys Glu Asn
        195                 200                 205

Ala Asp Arg Ala Val Gln Glu Phe Gly Ala Glu Phe Val His Pro Asp
    210                 215                 220

Lys Ile Tyr Asp Val Glu Cys Asp Ile Phe Ala Pro Cys Ala Leu Gly
225                 230                 235                 240

Ala Ile Ile Asn Asp Glu Thr Ile Glu Arg Leu Lys Cys Lys Val Val
                245                 250                 255

Ala Gly Ser Ala Asn Asn Gln Leu Lys Glu Glu Arg His Gly Lys Met
            260                 265                 270

Leu Glu Glu Lys Gly Ile Val Tyr Ala Pro Asp Tyr Val Ile Asn Ala
        275                 280                 285

Gly Gly Val Ile Asn Val Ala Asp Glu Leu Leu Gly Tyr Asn Arg Glu
```

```
    290                 295                 300

Arg Ala Met Lys Lys Val Glu Gly Ile Tyr Asp Lys Ile Leu Lys Val
305                 310                 315                 320

Phe Glu Ile Ala Lys Arg Asp Gly Ile Pro Ser Tyr Leu Ala Ala Asp
                325                 330                 335

Arg Met Ala Glu Glu Arg Ile Glu Met Met Arg Lys Thr Arg Ser Thr
            340                 345                 350

Phe Leu Gln Asp Gln Arg Asn Leu Ile Asn Phe Asn Asn Lys
        355                 360                 365


<210> SEQ ID NO 9
<211> LENGTH: 364
<212> TYPE: PRT
<213> ORGANISM: Bacillus subtilis

<400> SEQUENCE: 9

Met Glu Leu Phe Lys Tyr Met Glu Lys Tyr Asp Tyr Glu Gln Leu Val
1               5                   10                  15

Phe Cys Gln Asp Glu Gln Ser Gly Leu Lys Ala Ile Ile Ala Ile His
            20                  25                  30

Asp Thr Thr Leu Gly Pro Ala Leu Gly Gly Thr Arg Met Trp Thr Tyr
        35                  40                  45

Glu Asn Glu Glu Ala Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
            100                 105                 110

Ala Glu Asp Val Gly Thr Thr Val Glu Asp Met Asp Ile Ile His Asp
        115                 120                 125

Glu Thr Asp Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Ala Ala Phe Gly Thr Asp Ser Leu Glu Gly Lys Thr Ile
                165                 170                 175

Ala Val Gln Gly Val Gly Asn Val Ala Tyr Asn Leu Cys Arg His Leu
            180                 185                 190

His Glu Glu Gly Ala Asn Leu Ile Val Thr Asp Ile Asn Lys Gln Ser
        195                 200                 205

Val Gln Arg Ala Val Glu Asp Phe Gly Ala Arg Ala Val Asp Pro Asp
    210                 215                 220

Asp Ile Tyr Ser Gln Asp Cys Asp Ile Tyr Ala Pro Cys Ala Leu Gly
225                 230                 235                 240

Ala Thr Ile Asn Asp Asp Thr Ile Lys Gln Leu Lys Ala Lys Val Ile
                245                 250                 255

Ala Gly Ala Ala Asn Asn Gln Leu Lys Glu Thr Arg His Gly Asp Gln
            260                 265                 270

Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Ala Glu
    290                 295                 300
```

-continued

Arg Ala Leu Lys Lys Val Glu Gly Ile Tyr Gly Asn Ile Glu Arg Val
305 310 315 320

Leu Glu Ile Ser Gln Arg Asp Gly Ile Pro Ala Tyr Leu Ala Ala Asp
325 330 335

Arg Leu Ala Glu Glu Arg Ile Glu Arg Met Arg Arg Ser Arg Ser Gln
340 345 350

Phe Leu Gln Asn Gly His Ser Val Leu Ser Arg Arg
355 360

<210> SEQ ID NO 10
<211> LENGTH: 364
<212> TYPE: PRT
<213> ORGANISM: Bacillus licheniformis

<400> SEQUENCE: 10

Met Glu Leu Phe Arg Tyr Met Glu Gln Tyr Asp Tyr Glu Gln Leu Val
1 5 10 15

Phe Cys Gln Asp Lys Gln Ser Gly Leu Lys Ala Ile Ile Ala Ile His
20 25 30

Asp Thr Thr Leu Gly Pro Ala Leu Gly Gly Thr Arg Met Trp Thr Tyr
35 40 45

Glu Ser Glu Glu Ala Ala Ile Glu Asp Ala Leu Arg Leu Ala Arg Gly
50 55 60

Met Thr Tyr Lys Asn Ala Ala Ala Gly Leu Asn Leu Gly Gly Gly Lys
65 70 75 80

Thr Val Ile Ile Gly Asp Pro Arg Lys Asp Lys Asn Glu Glu Met Phe
85 90 95

Arg Ala Phe Gly Arg Tyr Ile Gln Gly Leu Asn Gly Arg Tyr Ile Thr
100 105 110

Ala Glu Asp Val Gly Thr Thr Val Glu Asp Met Asp Ile Ile His Asp
115 120 125

Glu Thr Asp Phe Val Thr Gly Ile Ser Pro Ala Phe Gly Ser Ser Gly
130 135 140

Asn Pro Ser Pro Val Thr Ala Tyr Gly Val Tyr Lys Gly Met Lys Ala
145 150 155 160

Ala Ala Lys Ala Ala Phe Gly Thr Asp Ser Leu Glu Gly Lys Thr Val
165 170 175

Ala Val Gln Gly Val Gly Asn Val Ala Tyr Asn Leu Cys Arg His Leu
180 185 190

His Glu Glu Gly Ala Lys Leu Ile Val Thr Asp Ile Asn Lys Glu Ala
195 200 205

Val Glu Arg Ala Val Ala Glu Phe Gly Ala Arg Ala Val Asp Pro Asp
210 215 220

Asp Ile Tyr Ser Gln Glu Cys Asp Ile Tyr Ala Pro Cys Ala Leu Gly
225 230 235 240

Ala Thr Ile Asn Asp Asp Thr Ile Pro Gln Leu Lys Ala Lys Val Ile
245 250 255

Ala Gly Ala Ala Asn Asn Gln Leu Lys Glu Thr Arg His Gly Asp Gln
260 265 270

Ile His Asp Met Gly Ile Val Tyr Ala Pro Asp Tyr Val Ile Asn Ala
275 280 285

Gly Gly Val Ile Asn Val Ala Asp Glu Leu Tyr Gly Tyr Asn Ser Glu
290 295 300

Arg Ala Leu Lys Lys Val Glu Gly Ile Tyr Gly Asn Ile Glu Arg Val
305 310 315 320

-continued

```
Leu Glu Ile Ser Lys Arg Asp Arg Ile Pro Thr Tyr Leu Ala Ala Asp
                325                 330                 335

Arg Leu Ala Glu Glu Arg Ile Glu Arg Met Arg Gln Ser Arg Ser Gln
            340                 345                 350

Phe Leu Gln Asn Gly His His Ile Leu Ser Arg Arg
        355                 360


<210> SEQ ID NO 11
<211> LENGTH: 367
<212> TYPE: PRT
<213> ORGANISM: Geobacillus stearothermophilus

<400> SEQUENCE: 11

Met Glu Leu Phe Lys Tyr Met Glu Thr Tyr Asp Tyr Glu Gln Val Leu
1               5                   10                  15

Phe Cys Gln Asp Lys Glu Ser Gly Leu Lys Ala Ile Ile Ala Ile His
            20                  25                  30

Asp Thr Thr Leu Gly Pro Ala Leu Gly Gly Thr Arg Met Trp Met Tyr
        35                  40                  45

Asn Ser Glu Glu Glu Ala Leu Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Ala Met Phe
                85                  90                  95

Arg Ala Phe Gly Arg Phe Ile Gln Gly Leu Asn Gly Arg Tyr Ile Thr
            100                 105                 110

Ala Glu Asp Val Gly Thr Thr Val Ala Asp Met Asp Ile Ile Tyr Gln
        115                 120                 125

Glu Thr Asp Tyr Val Thr Gly Ile Ser Pro Glu Phe Gly Ser Ser Gly
    130                 135                 140

Asn Pro Ser Pro Ala Thr Ala Tyr Gly Val Tyr Arg Gly Met Lys Ala
145                 150                 155                 160

Ala Ala Lys Glu Ala Phe Gly Ser Asp Ser Leu Glu Gly Lys Val Val
                165                 170                 175

Ala Val Gln Gly Val Gly Asn Val Ala Tyr His Leu Cys Arg His Leu
            180                 185                 190

His Glu Glu Gly Ala Lys Leu Ile Val Thr Asp Ile Asn Lys Glu Val
        195                 200                 205

Val Ala Arg Ala Val Glu Glu Phe Gly Ala Lys Ala Val Asp Pro Asn
    210                 215                 220

Asp Ile Tyr Gly Val Glu Cys Asp Ile Phe Ala Pro Cys Ala Leu Gly
225                 230                 235                 240

Gly Ile Ile Asn Asp Gln Thr Ile Pro Gln Leu Lys Ala Lys Val Ile
                245                 250                 255

Ala Gly Ser Ala Asp Asn Gln Leu Lys Glu Pro Arg His Gly Asp Ile
            260                 265                 270

Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
    290                 295                 300

Arg Ala Met Lys Lys Ile Glu Gln Ile Tyr Asp Asn Ile Glu Lys Val
305                 310                 315                 320

Phe Ala Ile Ala Lys Arg Asp Asn Ile Pro Thr Tyr Val Ala Ala Asp
```

```
                325                 330                 335

Arg Met Ala Glu Glu Arg Ile Glu Thr Met Arg Lys Ala Arg Ser Pro
            340                 345                 350

Phe Leu Gln Asn Gly His His Ile Leu Ser Arg Arg Arg Ala Arg
        355                 360                 365


<210> SEQ ID NO 12
<211> LENGTH: 364
<212> TYPE: PRT
<213> ORGANISM: Lysinibacillus sphaericus

<400> SEQUENCE: 12

Met Glu Ile Phe Lys Tyr Met Glu Lys Tyr Asp Tyr Glu Gln Leu Val
1               5                   10                  15

Phe Cys Gln Asp Glu Ala Ser Gly Leu Lys Ala Ile Ile Ala Ile His
            20                  25                  30

Asp Thr Thr Leu Gly Pro Ala Leu Gly Gly Ala Arg Met Trp Thr Tyr
        35                  40                  45

Ala Thr Glu Glu Asn Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Phe Lys Asp Lys Asn Glu Glu Met Phe
                85                  90                  95

Arg Ala Leu Gly Arg Phe Ile Gln Gly Leu Asn Gly Arg Tyr Ile Thr
            100                 105                 110

Ala Glu Asp Val Gly Thr Thr Val Thr Asp Met Asp Leu Ile His Glu
        115                 120                 125

Glu Thr Asn Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Glu Ala Phe Gly Thr Asp Met Leu Glu Gly Arg Thr Ile
                165                 170                 175

Ser Val Gln Gly Leu Gly Asn Val Ala Tyr Lys Leu Cys Glu Tyr Leu
            180                 185                 190

His Asn Glu Gly Ala Lys Leu Val Val Thr Asp Ile Asn Gln Ala Ala
        195                 200                 205

Ile Asp Arg Val Val Asn Asp Phe Gly Ala Thr Ala Val Ala Pro Asp
    210                 215                 220

Glu Ile Tyr Ser Gln Glu Val Asp Ile Phe Ser Pro Cys Ala Leu Gly
225                 230                 235                 240

Ala Ile Leu Asn Asp Glu Thr Ile Pro Gln Leu Lys Ala Lys Val Ile
                245                 250                 255

Ala Gly Ser Ala Asn Asn Gln Leu Gln Asp Ser Arg His Gly Asp Tyr
            260                 265                 270

Leu His Glu Leu Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
    290                 295                 300

Arg Ala Leu Lys Arg Val Asp Gly Ile Tyr Asp Ser Ile Glu Lys Ile
305                 310                 315                 320

Phe Glu Ile Ser Lys Arg Asp Ser Ile Pro Thr Tyr Val Ala Ala Asn
                325                 330                 335
```

```
Arg Leu Ala Glu Glu Arg Ile Ala Arg Val Ala Lys Ser Arg Ser Gln
            340                 345                 350

Phe Leu Lys Asn Glu Lys Asn Ile Leu Asn Gly Arg
        355                 360


<210> SEQ ID NO 13
<211> LENGTH: 351
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Any amino acid except Leu

<400> SEQUENCE: 13

Met Lys Tyr Ser Leu Asn Phe Lys Glu Ile Lys Ile Asp Asp Tyr Glu
1               5                   10                  15

Arg Val Ile Glu Val Thr Cys Ser Lys Val Arg Leu His Ala Ile Ile
            20                  25                  30

Ala Ile His Gln Thr Ala Val Gly Pro Ala Xaa Gly Gly Val Arg Ala
        35                  40                  45

Ser Leu Tyr Ser Ser Phe Glu Asp Ala Cys Thr Asp Ala Leu Arg Leu
    50                  55                  60

Ala Arg Gly Met Thr Tyr Lys Ala Ile Ile Ser Asn Thr Gly Thr Gly
65                  70                  75                  80

Gly Gly Lys Ser Val Ile Ile Leu Pro Gln Asp Ala Pro Ser Leu Thr
                85                  90                  95

Glu Asp Met Leu Arg Ala Phe Gly Gln Ala Val Asn Ala Leu Glu Gly
            100                 105                 110

Thr Tyr Ile Cys Ala Glu Asp Leu Gly Val Ser Ile Asn Asp Ile Ser
        115                 120                 125

Ile Val Ala Glu Glu Thr Pro Tyr Val Cys Gly Ile Ala Asp Val Ser
    130                 135                 140

Gly Asp Pro Ser Ile Tyr Thr Ala His Gly Gly Phe Leu Cys Ile Lys
145                 150                 155                 160

Glu Thr Ala Lys Tyr Leu Trp Gly Ser Ser Ser Leu Arg Gly Lys Lys
                165                 170                 175

Ile Ala Ile Gln Gly Ile Gly Ser Val Gly Arg Arg Leu Leu Gln Ser
            180                 185                 190

Leu Phe Phe Glu Gly Ala Glu Leu Tyr Val Ala Asp Val Leu Glu Arg
        195                 200                 205

Ala Val Gln Asp Ala Ala Arg Leu Tyr Gly Ala Thr Ile Val Pro Thr
    210                 215                 220

Glu Glu Ile His Ala Leu Glu Cys Asp Ile Phe Ser Pro Cys Ala Arg
225                 230                 235                 240

Gly Asn Val Ile Arg Lys Asp Asn Leu Ala Asp Leu Asn Cys Lys Ala
                245                 250                 255

Ile Val Gly Val Ala Asn Asn Gln Leu Glu Asp Ser Ser Ala Gly Met
            260                 265                 270

Met Leu His Glu Arg Gly Ile Leu Tyr Gly Pro Asp Tyr Leu Val Asn
        275                 280                 285

Ala Gly Gly Leu Leu Asn Val Ala Ala Ala Ile Glu Gly Arg Val Tyr
    290                 295                 300

Ala Pro Lys Glu Val Leu Leu Lys Val Glu Glu Leu Pro Ile Val Leu
```

-continued

```
305                 310                 315                 320

Ser Lys Leu Tyr Asn Gln Ser Lys Thr Thr Gly Lys Asp Leu Val Ala
                325                 330                 335

Leu Ser Asp Ser Phe Val Glu Asp Lys Leu Leu Ala Tyr Thr Ser
            340                 345                 350


<210> SEQ ID NO 14
<211> LENGTH: 366
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Any amino acid except Leu

<400> SEQUENCE: 14

Met Lys Ile Phe Asp Tyr Met Glu Lys Tyr Asp Tyr Glu Gln Leu Val
1               5                   10                  15

Met Cys Gln Asp Lys Glu Ser Gly Leu Lys Ala Ile Ile Cys Ile His
            20                  25                  30

Val Thr Thr Leu Gly Pro Ala Xaa Gly Gly Met Arg Met Trp Thr Tyr
        35                  40                  45

Ala Ser Glu Glu Glu Ala Ile Glu Asp Ala Leu Arg Leu Gly Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Ala Met Phe
                85                  90                  95

Arg Ala Leu Gly Arg Phe Ile Gln Gly Leu Asn Gly Arg Tyr Ile Thr
            100                 105                 110

Ala Glu Asp Val Gly Thr Thr Val Glu Asp Met Asp Ile Ile His Glu
        115                 120                 125

Glu Thr Arg Tyr Val Thr Gly Val Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Glu Ala Phe Gly Asp Asp Ser Leu Glu Gly Lys Val Val
                165                 170                 175

Ala Val Gln Gly Val Gly His Val Ala Tyr Glu Leu Cys Lys His Leu
            180                 185                 190

His Asn Glu Gly Ala Lys Leu Ile Val Thr Asp Ile Asn Lys Glu Asn
        195                 200                 205

Ala Asp Arg Ala Val Gln Glu Phe Gly Ala Glu Phe Val His Pro Asp
    210                 215                 220

Lys Ile Tyr Asp Val Glu Cys Asp Ile Phe Ala Pro Cys Ala Leu Gly
225                 230                 235                 240

Ala Ile Ile Asn Asp Glu Thr Ile Glu Arg Leu Lys Cys Lys Val Val
                245                 250                 255

Ala Gly Ser Ala Asn Asn Gln Leu Lys Glu Glu Arg His Gly Lys Met
            260                 265                 270

Leu Glu Glu Lys Gly Ile Val Tyr Ala Pro Asp Tyr Val Ile Asn Ala
        275                 280                 285

Gly Gly Val Ile Asn Val Ala Asp Glu Leu Leu Gly Tyr Asn Arg Glu
    290                 295                 300
```

```
Arg Ala Met Lys Lys Val Glu Gly Ile Tyr Asp Lys Ile Leu Lys Val
305                 310                 315                 320

Phe Glu Ile Ala Lys Arg Asp Gly Ile Pro Ser Tyr Leu Ala Ala Asp
                325                 330                 335

Arg Met Ala Glu Glu Arg Ile Glu Met Met Arg Lys Thr Arg Ser Thr
            340                 345                 350

Phe Leu Gln Asp Gln Arg Asn Leu Ile Asn Phe Asn Asn Lys
        355                 360                 365


<210> SEQ ID NO 15
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Any amino acid except Leu

<400> SEQUENCE: 15

Met Glu Leu Phe Lys Tyr Met Glu Lys Tyr Asp Tyr Glu Gln Leu Val
1               5                   10                  15

Phe Cys Gln Asp Glu Gln Ser Gly Leu Lys Ala Ile Ile Ala Ile His
            20                  25                  30

Asp Thr Thr Leu Gly Pro Ala Xaa Gly Gly Thr Arg Met Trp Thr Tyr
        35                  40                  45

Glu Asn Glu Glu Ala Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
            100                 105                 110

Ala Glu Asp Val Gly Thr Thr Val Glu Asp Met Asp Ile Ile His Asp
        115                 120                 125

Glu Thr Asp Tyr Val Thr Gly Ile Ser Pro Ala Phe Gly Ser Ser Gly
    130                 135                 140

Asn Pro Ser Pro Val Thr Ala Tyr Gly Val Tyr Arg Gly Met Lys Ala
145                 150                 155                 160

Ala Ala Lys Ala Ala Phe Gly Thr Asp Ser Leu Glu Gly Lys Thr Ile
                165                 170                 175

Ala Val Gln Gly Val Gly Asn Val Ala Tyr Asn Leu Cys Arg His Leu
            180                 185                 190

His Glu Glu Gly Ala Asn Leu Ile Val Thr Asp Ile Asn Lys Gln Ser
        195                 200                 205

Val Gln Arg Ala Val Glu Asp Phe Gly Ala Arg Ala Val Asp Pro Asp
    210                 215                 220

Asp Ile Tyr Ser Gln Asp Cys Asp Ile Tyr Ala Pro Cys Ala Leu Gly
225                 230                 235                 240

Ala Thr Ile Asn Asp Asp Thr Ile Lys Gln Leu Lys Ala Lys Val Ile
                245                 250                 255

Ala Gly Ala Ala Asn Asn Gln Leu Lys Glu Thr Arg His Gly Asp Gln
            260                 265                 270
```

-continued

```
Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Ala Glu
    290                 295                 300

Arg Ala Leu Lys Lys Val Glu Gly Ile Tyr Gly Asn Ile Glu Arg Val
305                 310                 315                 320

Leu Glu Ile Ser Gln Arg Asp Gly Ile Pro Ala Tyr Leu Ala Ala Asp
                325                 330                 335

Arg Leu Ala Glu Glu Arg Ile Glu Arg Met Arg Arg Ser Arg Ser Gln
            340                 345                 350

Phe Leu Gln Asn Gly His Ser Val Leu Ser Arg Arg
        355                 360


<210> SEQ ID NO 16
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Any amino acid except Leu

<400> SEQUENCE: 16

Met Glu Leu Phe Arg Tyr Met Glu Gln Tyr Asp Tyr Glu Gln Leu Val
1               5                   10                  15

Phe Cys Gln Asp Lys Gln Ser Gly Leu Lys Ala Ile Ile Ala Ile His
            20                  25                  30

Asp Thr Thr Leu Gly Pro Ala Xaa Gly Gly Thr Arg Met Trp Thr Tyr
        35                  40                  45

Glu Ser Glu Glu Ala Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Glu Met Phe
                85                  90                  95

Arg Ala Phe Gly Arg Tyr Ile Gln Gly Leu Asn Gly Arg Tyr Ile Thr
            100                 105                 110

Ala Glu Asp Val Gly Thr Thr Val Glu Asp Met Asp Ile Ile His Asp
        115                 120                 125

Glu Thr Asp Phe Val Thr Gly Ile Ser Pro Ala Phe Gly Ser Ser Gly
    130                 135                 140

Asn Pro Ser Pro Val Thr Ala Tyr Gly Val Tyr Lys Gly Met Lys Ala
145                 150                 155                 160

Ala Ala Lys Ala Ala Phe Gly Thr Asp Ser Leu Glu Gly Lys Thr Val
                165                 170                 175

Ala Val Gln Gly Val Gly Asn Val Ala Tyr Asn Leu Cys Arg His Leu
            180                 185                 190

His Glu Glu Gly Ala Lys Leu Ile Val Thr Asp Ile Asn Lys Glu Ala
        195                 200                 205

Val Glu Arg Ala Val Ala Glu Phe Gly Ala Arg Ala Val Asp Pro Asp
    210                 215                 220

Asp Ile Tyr Ser Gln Glu Cys Asp Ile Tyr Ala Pro Cys Ala Leu Gly
225                 230                 235                 240

Ala Thr Ile Asn Asp Asp Thr Ile Pro Gln Leu Lys Ala Lys Val Ile
```

```
                245                 250                 255

Ala Gly Ala Ala Asn Asn Gln Leu Lys Glu Thr Arg His Gly Asp Gln
            260                 265                 270

Ile His Asp Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Ser Glu
    290                 295                 300

Arg Ala Leu Lys Lys Val Glu Gly Ile Tyr Gly Asn Ile Glu Arg Val
305                 310                 315                 320

Leu Glu Ile Ser Lys Arg Asp Arg Ile Pro Thr Tyr Leu Ala Ala Asp
                325                 330                 335

Arg Leu Ala Glu Glu Arg Ile Glu Arg Met Arg Gln Ser Arg Ser Gln
            340                 345                 350

Phe Leu Gln Asn Gly His His Ile Leu Ser Arg Arg
        355                 360


<210> SEQ ID NO 17
<211> LENGTH: 367
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Any amino acid except Leu

<400> SEQUENCE: 17

Met Glu Leu Phe Lys Tyr Met Glu Thr Tyr Asp Tyr Glu Gln Val Leu
1               5                   10                  15

Phe Cys Gln Asp Lys Glu Ser Gly Leu Lys Ala Ile Ile Ala Ile His
            20                  25                  30

Asp Thr Thr Leu Gly Pro Ala Xaa Gly Gly Thr Arg Met Trp Met Tyr
        35                  40                  45

Asn Ser Glu Glu Glu Ala Leu Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Arg Lys Asp Lys Asn Glu Ala Met Phe
                85                  90                  95

Arg Ala Phe Gly Arg Phe Ile Gln Gly Leu Asn Gly Arg Tyr Ile Thr
            100                 105                 110

Ala Glu Asp Val Gly Thr Thr Val Ala Asp Met Asp Ile Ile Tyr Gln
        115                 120                 125

Glu Thr Asp Tyr Val Thr Gly Ile Ser Pro Glu Phe Gly Ser Ser Gly
    130                 135                 140

Asn Pro Ser Pro Ala Thr Ala Tyr Gly Val Tyr Arg Gly Met Lys Ala
145                 150                 155                 160

Ala Ala Lys Glu Ala Phe Gly Ser Asp Ser Leu Glu Gly Lys Val Val
                165                 170                 175

Ala Val Gln Gly Val Gly Asn Val Ala Tyr His Leu Cys Arg His Leu
            180                 185                 190

His Glu Glu Gly Ala Lys Leu Ile Val Thr Asp Ile Asn Lys Glu Val
        195                 200                 205

Val Ala Arg Ala Val Glu Glu Phe Gly Ala Lys Ala Val Asp Pro Asn
    210                 215                 220
```

```
Asp Ile Tyr Gly Val Glu Cys Asp Ile Phe Ala Pro Cys Ala Leu Gly
225                 230                 235                 240

Gly Ile Ile Asn Asp Gln Thr Ile Pro Gln Leu Lys Ala Lys Val Ile
                245                 250                 255

Ala Gly Ser Ala Asp Asn Gln Leu Lys Glu Pro Arg His Gly Asp Ile
            260                 265                 270

Ile His Glu Met Gly Ile Val Tyr Ala Pro Asp Tyr Val Ile Asn Ala
        275                 280                 285

Gly Gly Val Ile Asn Val Ala Asp Glu Leu Tyr Gly Tyr Asn Arg Glu
    290                 295                 300

Arg Ala Met Lys Lys Ile Glu Gln Ile Tyr Asp Asn Ile Glu Lys Val
305                 310                 315                 320

Phe Ala Ile Ala Lys Arg Asp Asn Ile Pro Thr Tyr Val Ala Ala Asp
                325                 330                 335

Arg Met Ala Glu Glu Arg Ile Glu Thr Met Arg Lys Ala Arg Ser Pro
            340                 345                 350

Phe Leu Gln Asn Gly His His Ile Leu Ser Arg Arg Arg Ala Arg
        355                 360                 365


<210> SEQ ID NO 18
<211> LENGTH: 364
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (40)..(40)
<223> OTHER INFORMATION: Any amino acid except Leu

<400> SEQUENCE: 18

Met Glu Ile Phe Lys Tyr Met Glu Lys Tyr Asp Tyr Glu Gln Leu Val
1               5                   10                  15

Phe Cys Gln Asp Glu Ala Ser Gly Leu Lys Ala Ile Ile Ala Ile His
            20                  25                  30

Asp Thr Thr Leu Gly Pro Ala Xaa Gly Gly Ala Arg Met Trp Thr Tyr
        35                  40                  45

Ala Thr Glu Glu Asn Ala Ile Glu Asp Ala Leu Arg Leu Ala Arg Gly
    50                  55                  60

Met Thr Tyr Lys Asn Ala Ala Ala Gly Leu Asn Leu Gly Gly Gly Lys
65                  70                  75                  80

Thr Val Ile Ile Gly Asp Pro Phe Lys Asp Lys Asn Glu Glu Met Phe
                85                  90                  95

Arg Ala Leu Gly Arg Phe Ile Gln Gly Leu Asn Gly Arg Tyr Ile Thr
            100                 105                 110

Ala Glu Asp Val Gly Thr Thr Val Thr Asp Met Asp Leu Ile His Glu
        115                 120                 125

Glu Thr Asn Tyr Val Thr Gly Ile Ser Pro Ala Phe Gly Ser Ser Gly
    130                 135                 140
```

Asn Pro Ser Pro Val Thr Ala Tyr Gly Val Tyr Arg Gly Met Lys Ala
145 150 155 160

Ala Ala Lys Glu Ala Phe Gly Thr Asp Met Leu Glu Gly Arg Thr Ile
165 170 175

Ser Val Gln Gly Leu Gly Asn Val Ala Tyr Lys Leu Cys Glu Tyr Leu
180 185 190

His Asn Glu Gly Ala Lys Leu Val Val Thr Asp Ile Asn Gln Ala Ala
195 200 205

Ile Asp Arg Val Val Asn Asp Phe Gly Ala Thr Ala Val Ala Pro Asp
210 215 220

Glu Ile Tyr Ser Gln Glu Val Asp Ile Phe Ser Pro Cys Ala Leu Gly
225 230 235 240

Ala Ile Leu Asn Asp Glu Thr Ile Pro Gln Leu Lys Ala Lys Val Ile
245 250 255

Ala Gly Ser Ala Asn Asn Gln Leu Gln Asp Ser Arg His Gly Asp Tyr
260 265 270

Leu His Glu Leu Gly Ile Val Tyr Ala Pro Asp Tyr Val Ile Asn Ala
275 280 285

Gly Gly Val Ile Asn Val Ala Asp Glu Leu Tyr Gly Tyr Asn Arg Glu
290 295 300

Arg Ala Leu Lys Arg Val Asp Gly Ile Tyr Asp Ser Ile Glu Lys Ile
305 310 315 320

Phe Glu Ile Ser Lys Arg Asp Ser Ile Pro Thr Tyr Val Ala Ala Asn
325 330 335

Arg Leu Ala Glu Glu Arg Ile Ala Arg Val Ala Lys Ser Arg Ser Gln
340 345 350

Phe Leu Lys Asn Glu Lys Asn Ile Leu Asn Gly Arg
355 360

<210> SEQ ID NO 19
<211> LENGTH: 3
<212> TYPE: PRT
<213> ORGANISM: Unknown
<220> FEATURE:
<223> OTHER INFORMATION: Description of Unknown: bacterial leucine dehydrogenase conserved region peptide

<400> SEQUENCE: 19

Asn Val Ala
1

<210> SEQ ID NO 20
<211> LENGTH: 366
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

Met Thr Leu Glu Ile Phe Glu Tyr Leu Glu Lys Tyr Asp Tyr Glu Gln
1 5 10 15

Val Val Phe Cys Gln Asp Lys Glu Ser Gly Leu Lys Ala Ile Ile Ala
20 25 30

-continued

```
Ile His Asp Thr Thr Leu Gly Pro Ala Ala Gly Gly Thr Arg Met Trp
        35                  40                  45

Thr Tyr Asp Ser Glu Glu Ala Ala Ile Glu Asp Ala Leu Arg Leu Ala
    50                  55                  60

Lys Gly Met Thr Tyr Lys Asn Ala Ala Ala Gly Leu Asn Leu Gly Gly
65                  70                  75                  80

Ala Lys Thr Val Ile Ile Gly Asp Pro Arg Lys Asp Lys Ser Glu Ala
                85                  90                  95

Met Phe Arg Ala Leu Gly Arg Tyr Ile Gln Gly Leu Asn Gly Arg Tyr
            100                 105                 110

Ile Thr Ala Glu Asp Val Gly Thr Thr Val Asp Asp Met Asp Ile Ile
        115                 120                 125

His Glu Glu Thr Asp Phe Val Thr Gly Ile Ser Pro Ser Phe Gly Ser
    130                 135                 140

Ser Gly Asn Pro Ser Pro Val Thr Ala Tyr Gly Val Tyr Arg Gly Met
145                 150                 155                 160

Lys Ala Ala Ala Lys Glu Ala Phe Gly Thr Asp Asn Leu Glu Gly Lys
                165                 170                 175

Val Ile Ala Val Gln Gly Val Gly Asn Val Ala Tyr His Leu Cys Lys
            180                 185                 190

His Leu His Ala Glu Gly Ala Lys Leu Ile Val Thr Asp Ile Asn Lys
        195                 200                 205

Glu Ala Val Gln Arg Ala Val Glu Glu Phe Gly Ala Ser Ala Val Glu
    210                 215                 220

Pro Asn Glu Ile Tyr Gly Val Glu Cys Asp Ile Tyr Ala Pro Cys Ala
225                 230                 235                 240

Leu Gly Ala Thr Val Asn Asp Glu Thr Ile Pro Gln Leu Lys Ala Lys
                245                 250                 255

Val Ile Ala Gly Ser Ala Asn Asn Gln Leu Lys Glu Asp Arg His Gly
            260                 265                 270

Asp Ile Ile His Glu Met Gly Ile Val Tyr Ala Pro Asp Tyr Val Ile
        275                 280                 285

Asn Ala Gly Gly Val Ile Asn Val Ala Asp Glu Leu Tyr Gly Tyr Asn
    290                 295                 300

Arg Glu Arg Ala Leu Lys Arg Val Glu Ser Ile Tyr Asp Thr Ile Ala
305                 310                 315                 320

Lys Val Ile Glu Ile Ser Lys Arg Asp Gly Ile Ala Thr Tyr Val Ala
                325                 330                 335

Ala Asp Arg Leu Ala Glu Glu Arg Ile Ala Ser Leu Lys Asn Ser Arg
            340                 345                 350

Ser Thr Tyr Leu Arg Asn Gly His Asp Ile Ile Ser Arg Arg
        355                 360                 365
```